(12) United States Patent
Nahlieli et al.

(10) Patent No.: US 8,366,443 B2
(45) Date of Patent: Feb. 5, 2013

(54) DENTAL IMPLANTS, DEVICES AND METHODS ASSOCIATED WITH DENTAL IMPLANTATION PROCEDURES

(75) Inventors: Oded Nahlieli, Ashkelon (IL); Itzhak Henig, Ashkelon (IL)

(73) Assignee: Sialo-Lite Ltd., Ashkelon (IL)

( * ) Notice: Subject to any disclaimer, the term of this patent is extended or adjusted under 35 U.S.C. 154(b) by 5 days.

(21) Appl. No.: 12/656,341

(22) Filed: Jan. 26, 2010

(65) Prior Publication Data

US 2010/0196841 A1  Aug. 5, 2010

Related U.S. Application Data

(63) Continuation-in-part of application No. 12/461,626, filed on Aug. 18, 2009.

(51) Int. Cl.
*A61C 13/12* (2006.01)

(52) U.S. Cl. .................................................. 433/172

(58) Field of Classification Search .......... 433/172–174, 433/180, 226
See application file for complete search history.

(56) References Cited

U.S. PATENT DOCUMENTS

| | | | |
|---|---|---|---|
| 612,662 A | 10/1898 | Detwiler | |
| 3,807,048 A | 4/1974 | Malmin | |
| 4,671,768 A | 6/1987 | Ton | |
| 5,503,559 A | 4/1996 | Vari | |
| 5,662,586 A | 9/1997 | Monroe et al. | |
| 5,711,315 A * | 1/1998 | Jerusalmy | 128/898 |
| 5,800,165 A * | 9/1998 | Kirsch et al. | 433/29 |
| 5,999,687 A | 12/1999 | Abraham et al. | |
| 6,013,025 A | 1/2000 | Bonne et al. | |
| 6,042,380 A | 3/2000 | De Rowe | |
| 6,093,183 A | 7/2000 | Pavkovich | |
| 6,162,052 A | 12/2000 | Kokubu | |
| 6,270,342 B1 * | 8/2001 | Neuberger et al. | 433/29 |
| 6,458,120 B1 | 10/2002 | Shen et al. | |
| 6,635,011 B1 * | 10/2003 | Ozawa et al. | 600/178 |
| 6,679,837 B2 * | 1/2004 | Daikuzono | 600/157 |
| 6,799,970 B2 | 10/2004 | Martin et al. | |
| 6,840,770 B2 | 1/2005 | McDevitt | |
| 7,125,253 B2 * | 10/2006 | Kitamura et al. | 433/173 |
| 7,510,397 B2 | 3/2009 | Hochman | |
| 7,934,929 B2 * | 5/2011 | Better et al. | 433/174 |

(Continued)

FOREIGN PATENT DOCUMENTS

| | | |
|---|---|---|
| DE | 44 04 983 A1 | 9/1994 |
| DE | 43 21 785 C1 | 3/1995 |

(Continued)

OTHER PUBLICATIONS

International Search Report, PCT/IL2010/000900, mailed on Mar. 15, 2011.

(Continued)

*Primary Examiner* — Cris L Rodriguez
*Assistant Examiner* — Matthew Saunders
(74) *Attorney, Agent, or Firm* — Vorys, Sater, Seymour and Pease LLP; Susanne M. Hopkins; William L. Klima

(57) ABSTRACT

A dental implant installation procedure is provided in which a distal end of a dental implant is projected into a paranasal sinus cavity or a nasal cavity to thereby displace the respective sinus membrane or nasal cavity membrane from the respective cavity floor, while minimizing risk of damaging the respective membrane. Bone graft material is introduced into the space thereby created between the respective membrane and the respective cavity floor via a distal portion of the dental implant to thereby form a desired sinus augmentation.

16 Claims, 9 Drawing Sheets

U.S. PATENT DOCUMENTS

| | | | |
|---|---|---|---|
| 2002/0177102 A1* | 11/2002 | Martin et al. | 433/173 |
| 2003/0105469 A1* | 6/2003 | Karmon | 606/92 |
| 2003/0124486 A1 | 7/2003 | McDevitt | |
| 2004/0073374 A1 | 4/2004 | Lockhart et al. | |
| 2004/0162572 A1 | 8/2004 | Sauer | |
| 2006/0084034 A1* | 4/2006 | Hochman | 433/173 |
| 2006/0172255 A1* | 8/2006 | Hochman et al. | 433/144 |
| 2006/0235273 A1* | 10/2006 | Moriyama et al. | 600/113 |
| 2007/0225695 A1* | 9/2007 | Mayer et al. | 606/15 |
| 2008/0108011 A1* | 5/2008 | Nahlieli | 433/29 |
| 2008/0215010 A1 | 9/2008 | Silver et al. | |
| 2008/0319466 A1* | 12/2008 | Eder | 606/169 |
| 2009/0208907 A1 | 8/2009 | Dosta et al. | |
| 2009/0318912 A1* | 12/2009 | Mayer et al. | 606/14 |
| 2010/0081112 A1 | 4/2010 | Better et al. | |

FOREIGN PATENT DOCUMENTS

| | | |
|---|---|---|
| DE | 102008016082 A1 * | 10/2008 |
| EP | 0 830 852 A1 | 3/1998 |
| EP | 1195146 A1 | 4/2002 |
| JP | 7-222752 A | 8/1995 |
| RU | 2 199 970 C2 | 3/2003 |
| WO | 2005/055817 A1 | 6/2005 |
| WO | 2007005614 A2 | 1/2007 |
| WO | WO 2007005614 A2 * | 1/2007 |
| WO | 2009/024107 A1 | 2/2009 |

OTHER PUBLICATIONS

The International Search Report for corresponding International PCT Application No. PCT/IL2011/000083; two pages; search completed on Jun. 8, 2011.

* cited by examiner

DENTAL IMPLANTS, DEVICES AND METHODS ASSOCIATED WITH DENTAL IMPLANTATION PROCEDURES

This application claims the benefit under 35 U.S.C.§120 of prior U.S. patent application Ser. No. 12/461,626, filed on Aug. 18, 2009, the content of which is hereby incorporated by reference in its entirety.

FIELD OF THE INVENTION

This invention relates to dental implants, devices, systems and methods for use in procedures associated with the intra-oral cavity, in particular with respect to dental implant procedures, to sinus augmentation procedures and to nasal augmentation procedures.

BACKGROUND OF THE INVENTION

Conventional dental implant procedures for the upper jaw or maxilla sometimes requires a sinus augmentation procedure to be first implemented, so as to provide sufficient bone to anchor the implant. A commonly used sinus augmentation procedure is performed from inside the intraoral cavity. In what is known as the lateral approach, a lateral incision is made into the gum and gum tissue is pulled back, and an opening is cut in the exposed lateral boney wall of the sinus. The sinus is covered by a thin membrane, which is lifted away to create a space into which allogenic, autogenous, or synthetic bone graft material is inserted via the opening. However, cutting through the honey wall and lifting the membrane can lead to tearing or puncturing of the membrane if not done carefully, and this requires the membrane to be immediately repaired, postponing the sinus augmentation procedure until healing of the membrane is complete. Once the bone graft material has been is integrated in the maxilla, which can normally take between 6 and 12 months, the dental implant can be installed, followed by the dental prosthesis.

Another method sometime used when there is a minimum of 5 mm involves inserting the bone graft material from the crest of the bone during implant placement, and is known as the crestal approach. The normal implant hole is drilled until about 1 mm before the sinus, and then another tool is used for taping the remaining shell of bone towards the sinus. The tapped shell displaces the membrane into the sinus, making room for the graft material which is then inserted via the implant hole. The implant is then installed into the prepared bone, allowing the graft material to become integrated while anchoring the implant.

By way of general background, US 2009/208907 is directed to a group of dental implants used for two-stage implantation into the alveolar bone.

US 2003/124486 discloses systems and methods for a dental implant system suitable for an endosteal implant into a jawbone. The systems and methods make use of a tapered, expandable polymer sheath insertable into a jawbone, a tapered implant insertable into the sheath and causing expansion of the sheath upon insertion, and an abutment adapted to be coupled to the implant and permitting the attachment of a dental prosthesis.

U.S. Pat. No. 7,510,397 discloses a method and apparatus for providing implants in the upper jaws of a person. A sleeve is inserted through the alveolar ridge to the maxillary sinus. The sleeve is used to initiate separation of the subantral membrane and this is followed by hydrodissection using fluid pressure to form a cavity, with the sleeve remaining in place. A filler, such as a bone growth stimulant is injected through the sleeve into the cavity.

US 2002/177102 discloses a dental implant for anchoring in a bone structure comprising a head intended to support a dental prosthesis and a threaded root of cylindrical substance, in which the threaded root has an internal cavity and a lateral orifice through which this internal cavity opens out on the external lateral face of the root. The axial position of this orifice is such that when the implant is in position, this orifice opens out on a medullary zone of the bone structure.

U.S. Pat. No. 6,042,380 discloses an expandable dental implant which can immediately receive functional loading to support a dental prosthesis upon insertion into the patient's mouth. The expandable implant is constructed as an inflatable balloon.

DE 4321785 discloses a dental implant having a balloon which can be inserted, in particular, in tooth sockets, jaw cavities or artificially created bone cavities, can be filled via a closable filling opening with gas, liquid and/or solid filler materials, can be attached to the jaw or tooth in the region of its filling opening and is provided with an outer layer which can grow on in the bone cavity to be filled.

U.S. Pat. No. 4,671,768 discloses an implant comprising an anchoring part having one or more fixing means as well as a prosthesis part adapted to fix a dental prosthesis, which implant is provided with a cavity extending from the prosthesis part into the anchoring part, the wall of the anchoring part is perforated at one or more spots and the prosthesis part is provided with a removable closing means for the cavity; when the implant is implanted the cavity of the implant may contain a medicine for protecting the implant against pathogenic bacteria etc.

Further by way of general background, WO 2009/024107 discloses a modular endoscope system in which a plurality of connecting pieces, tools and cannulas are assigned to a single lens and are each selected according to the use thereof. The connecting pieces and the cannulas are said to be designed preferably for single use so that only the lens must be decontaminated.

SUMMARY OF THE INVENTION

According to one aspect of the invention, there is provided a method for implanting a dental implant in a maxilla of a dental patient, the maxilla having a paranasal sinus cavity lined with a sinus membrane, the method comprising:
  (a) providing the implant, the implant comprising a proximal portion configured for enabling a prosthesis to be mounted thereto and having at least one proximal opening, and a distal portion having a distal end and at least one distal opening at or in proximity to said distal end, said distal portion configured for being implanted with respect to the maxilla, and further comprising at least one internal passage providing fluid communication between said at least one proximal opening and said at least one distal opening;
  (b) forming a channel through the alveolar ridge of the maxilla, extending from an outside of the maxilla to the sinus floor of the maxilla;
  (c) installing the dental implant in the maxilla by inserting the implant via said channel, and concurrently creating a first space between the sinus floor and the sinus membrane, wherein at least a majority of said first space is formed by the distal displacement of said sinus membrane responsive to said distal end being incrementally projected in a direction towards the sinus cavity until the implant is substantially fully seated in its required final position with respect to the alveolar ridge, and wherein fluid communication between the outside of the maxilla and said first space is provided via said at least one passage and said at least one distal opening; and (d) providing via at least one internal passage and said at least one distal opening suitable bone graft material to said first space to form a sinus augmentation.

Alternatively, step (c) comprises installing the dental implant in the maxilla by inserting the implant via said channel, and concurrently creating a first space between the sinus floor and the sinus membrane by displacing said sinus membrane from said sinus floor, wherein at least a majority of said sinus displacement is responsive to said distal end being incrementally projected in a direction towards the sinus cavity in abutment with said sinus membrane, and wherein fluid communication between the outside of the maxilla and said first space is provided via said at least one passage and said at least one distal opening.

The method may further comprise the step of allowing the dental implant to be anchored in situ in said sinus augmentation.

In at least some embodiments, said distal end may comprise a blunt abutment portion that is in abutting contact with said sinus membrane at least during a majority of the displacement of said sinus membrane.

In at least some embodiments, in step (d) sufficient said bone graft material is provided to further displace said sinus membrane wherein to augment said first space with a second space that is at least partially filled with said bone graft material, wherein said sinus augmentation also includes said at least partially filled second space.

In at least some embodiments, the method further comprises the step of sealing said at least one internal passage.

In at least some embodiments, the method further comprises the step of mounting a suitable prosthesis to said implant.

In at least some embodiments, step (b) comprises:
(b1) forming a window in the gingival of the maxilla;
(b2) using a working end of a first tool, removing material from the bone of the alveolar ridge of the maxilla to form said channel extending from said window to said sinus floor, while monitoring said material removal process via a suitable image acquisition system.

Typically, in step (a), said window is formed on a crest portion of the gum.

Optionally, said first tool and said image acquisition unit are included in a suitable device, wherein said image acquisition unit and said tool working end are positioned in the device such said tool working end is in the field of view of said image acquisition unit at least during operation of the first tool. Further optionally, said device is hand-manipulated by the user at least during part of step (b2). Further optionally, step (d) comprises injecting said bone graft material using a second tool included in said device; said second tool may optionally be provided in the form of a syringe having a respective second tool working end in the form of a delivery hose having a distal opening, and wherein said second tool is used for injecting said bone graft material into said first space via said needle opening, and wherein said injection process is monitored in real time via said image acquisition system.

In at least some embodiments, said at least one internal passage provides a direct line of sight between said at least one proximal opening and said at least one distal opening. The method may further comprise monitoring in real time said displacement of the sinus membrane using an image acquisition system, wherein a part of the sinus membrane in abutment with or in proximity to said distal end is in the field of view of said image acquisition system. In at least some embodiments, the at least one said distal opening is at said distal end and said part of the sinus membrane in abutment with or in proximity to said distal end is in the field of view of said image acquisition unit via said distal opening at said distal end. In at least some embodiments, said distal end is transparent and said part of the sinus membrane in abutment with or in proximity to said distal end is in the field of view of said image acquisition unit via said transparent distal end.

In at least some embodiments, the method further comprises monitoring a color of said part of the sinus membrane and halting the displacement of said sinus membrane when said color is considered to have blanched.

The method may optionally further comprise sealing said at least one passage.

The method according to this aspect of the invention may be extended to a number of implants concurrently implanted in the maxilla with respect to a common sinus cavity. According to such an embodiment, there is provided a method for implanting at least two dental implants in a maxilla of a dental patient, the maxilla having a paranasal sinus cavity lined with a sinus membrane, the method comprising:

(A) providing the at least two implants, each said implant comprising a proximal portion configured for enabling a prosthesis to be mounted thereto and having at least one proximal opening, and wherein at least one said implant comprises a distal portion having a distal end and at least one distal opening at or in proximity to said distal end, said distal portion configured for being implanted with respect to the maxilla and further comprising at least one internal passage providing fluid communication between said at least one proximal opening and said at least one distal opening;

(B) for each said implant, forming a respective channel through the alveolar ridge of the maxilla, extending from an outside of the maxilla to the sinus floor of the maxilla;

(C) installing the dental implants in the maxilla by inserting each implant via the respective said channel, and concurrently creating a first space between the sinus floor and the sinus membrane by displacing said sinus membrane from said sinus floor, wherein at least a majority of said sinus displacement is responsive to each said distal end being incrementally projected in a direction towards the sinus cavity in abutment with said sinus membrane, and wherein fluid communication between the outside of the maxilla and said first space is provided via said at least one passage and said at least one distal opening for each said dental implant; and (D) providing via at least one internal passage and said at least one distal opening suitable bone graft material to said first space to form a sinus augmentation.

Alternatively, step (C) comprises installing the dental implant in the maxilla by inserting the implant via said channel, and concurrently creating a first space between the sinus floor and the sinus membrane, wherein at least a majority of said first space is formed by the distal displacement of said sinus membrane responsive to said distal end being incrementally projected in a direction towards the sinus cavity until the implant is substantially fully seated in its required final position with respect to the alveolar ridge, and wherein fluid communication between the outside of the maxilla and said first space is provided via said at least one passage and said at least one distal opening.

Optionally, each implant may comprise a passageway to the distal end thereof, so that suitable bone graft material may be provided via each implant to the space.

The above methods and variations thereof may be applied, mutatis mutandis, to implanting one or more dental implants with respect to a nasal cavity lined with a membrane, rather than the aforesaid paranasal sinus cavity lined with a sinus membrane.

According to other embodiments of the invention, there is provided a dental implant installation procedure wherein a distal end of a dental implant is projected into one of the paranasal sinus cavity and the nasal cavity to thereby directly displace the respective sinus membrane or nasal cavity membrane from the respective cavity floor and thereby form a space between the respective membrane and the respective cavity floor, while minimizing risk of damaging the respective membrane, and introducing bone graft material into said space via a distal portion of the dental implant to form a sinus augmentation. The implant abuttingly contacts and displaces the respective membrane until the implant is fully seated in the bone, after which said bone graft material is introduced into said space.

According to this aspect of the invention, there is also provided a method for implanting a dental implant in a mandible of a dental patient:
 (a) providing the implant, the implant comprising a proximal portion configured for enabling a prosthesis to be mounted thereto and having at least one proximal opening, and a distal portion having a distal end, said distal portion configured for being implanted with respect to the mandible, and further comprising at least one internal passage providing at least optical communication between said at least one proximal opening and said distal end, wherein said distal end is configured for enabling a distal outside of said distal end to be observed via the distal end;
 (b) forming a channel through a portion of the depth of the mandible, extending from an outside of the mandible;
 (c) installing the dental implant in the mandible by inserting the implant via said channel, and concurrently monitoring said implant installation via said distal end.

According to another aspect of the invention, there is provided a dental implant for use in a maxilla, comprising a proximal portion configured for enabling a prosthesis to be mounted thereto and having at least one proximal opening, and a distal portion having a distal end and at least one distal opening at or in proximity to said distal end, said distal portion configured for being implanted with respect to the maxilla, and further comprising at least one internal passage providing fluid communication between said at least one proximal opening and said at least one distal opening, wherein said distal end is configured for projecting into a sinus cavity and for directly displacing at least a majority of the corresponding sinus membrane during installation of the dental implant in the maxilla to thereby a create a space between said sinus membrane and a corresponding sinus floor corresponding to a required sinus augmentation, while providing fluid communication between said at least one distal opening and at least one of said sinus portion and said space.

The said at least one distal opening and said at least one passage may be configured for enabling suitable bone graft material to be inserted therethrough to form said sinus augmentation while the dental implant is installed in the maxilla.

The distal end is devoid of sharp or cutting elements that could otherwise damage the sinus membrane if in contact therewith.

Optionally, said distal end is transparent, wherein said proximal opening and said passage are aligned with a longitudinal axis of the dental implant, and wherein said distal portion comprises one or a plurality of said distal openings proximally displaced from said distal end and laterally disposed with respect to said passage.

The proximal opening and said passage may be aligned with a longitudinal axis of the dental implant, and said distal portion may further comprise one or a plurality of additional said distal openings proximally displaced from said distal end and laterally disposed with respect to said passage.

The distal end may comprise a blunt abutment portion configured for abutting contact with said sinus membrane.

The dental implant may further comprise a plug member for selectively sealing said passage.

The distal portion may comprises an external screwthread structure for affixing said distal portion in the alveolar bone of the maxilla.

According to this aspect of the invention, there is also provided a dental implant for use in a mandible, comprising a proximal portion configured for enabling a prosthesis to be mounted thereto and having at least one proximal opening, and a distal portion having a distal end, said distal portion configured for being implanted with respect to the mandible, and further comprising at least one internal passage providing at least optical communication between said at least one proximal opening and said distal end, wherein said distal end is configured for enabling a distal outside of said distal end to be observed via the distal end to at least allow monitoring of said implant installation via said distal end.

BRIEF DESCRIPTION OF THE DRAWINGS

In order to understand the invention and to see how it may be carried out in practice, embodiments will now be described, by way of non-limiting example only, with reference to the accompanying drawings, in which:

FIG. 1a illustrates one mode of operation of the tip of the embodiment of FIG. 1.

DETAILED DESCRIPTION OF EMBODIMENTS

According to a first aspect of the invention, there is provided a device for carrying out a variety of procedures, including dental procedures, and in particular dental implant procedures and sinus augmentation procedures, as will become clearer herein.

Herein the term "distal" (D) herein refers to a direction generally away from the user of the device, while the term "proximal" (P) refers to a direction opposed to distal, that is, a direction generally towards the user of the device. Additionally or alternatively, the distal direction (D) herein refers to a general direction from the intra-oral cavity towards the inside of the maxilla of the dental patient, while the proximal direction (P) is in a direction opposed to the distal direction.

Figure 1:
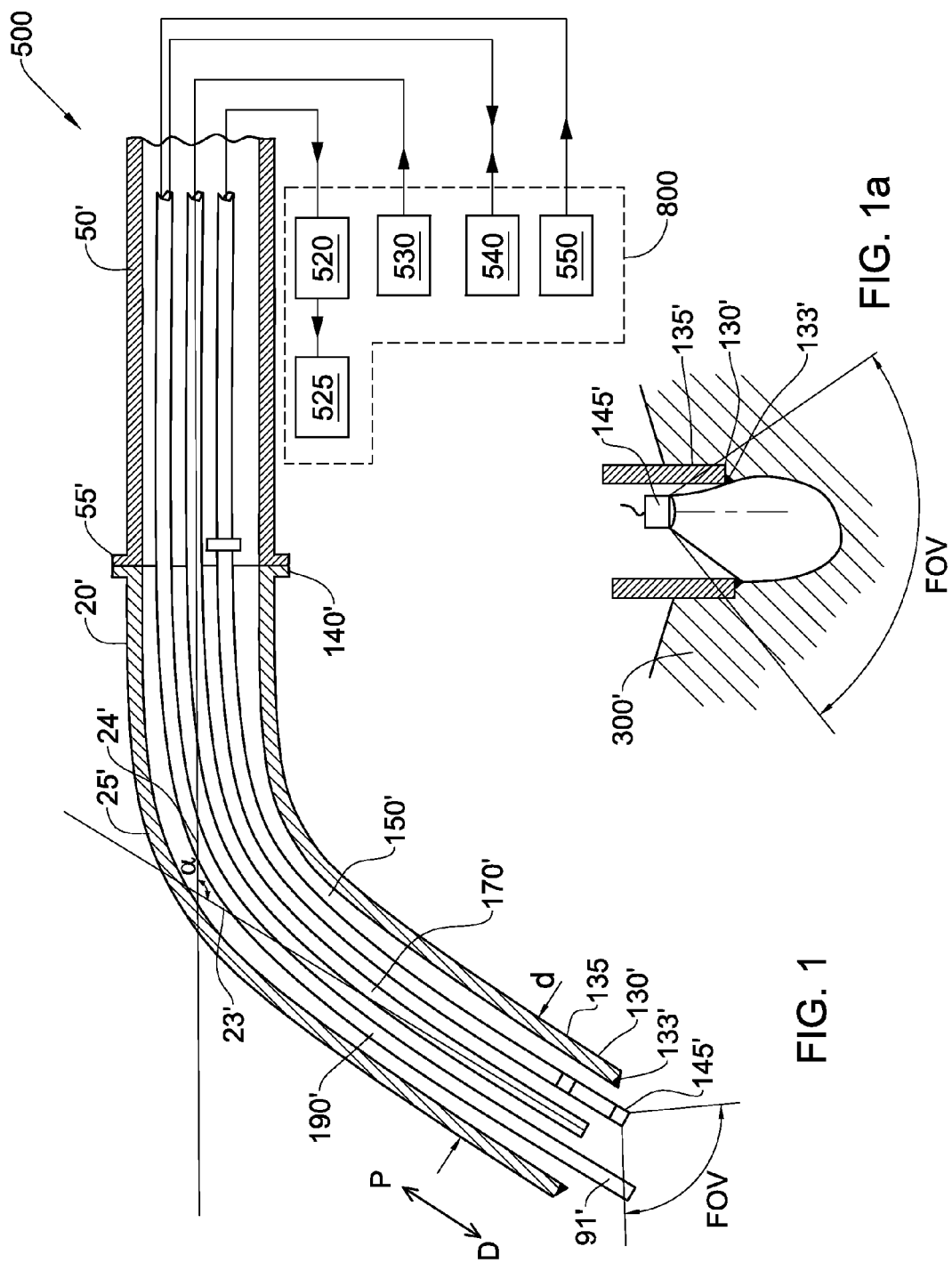
FIG. 1 illustrates, in transverse cross-sectional view, a device according to an embodiment of the invention.

Referring to FIG. 1 and FIG. 1a, an embodiment of the device according to the first aspect of the invention, generally designated 500, comprises handpiece 50' and a probe member 20' axially mounted thereto and connected to the handpiece 50' via a Luer lock, bayonet fit or any other suitable connection 55'. The probe member 20' has an elbow 25' to define angle α between the central axis 23' of the probe at the distal end 130' and the central axis 24' at the proximal end 140', which is co-axial with the longitudinal axis of the handpiece 50'. The probe member 20' has a central passageway 150' between the open distal end 130' and the open proximal end 140'. Passageway 150' extends through handpiece 50' and collectively functions as: (a) a treatment channel for accommodating one or more tools; (b) as an illumination channel for accommodating an illumination arrangement for illuminating the area being worked on by such tool or tools; and (c) as a light collection channel for acquiring images of this area. The device 500 thus further comprises an image acquisition unit 145', which in this embodiment may comprise a CCD or the like, accommodated at or near the distal end of the distal portion 135' of the probe member 20', and operatively connected, for example via cables, to a suitable image acquisition system 520, which may also be configured for displaying images thereby acquired via a suitable image analysis and display unit 525. In at least some such embodiments, the CCD may be disposable together with at least the probe member 20' after use of the device 500 with a patient.

The image acquisition unit 145' comprises a field of view (FOV), and the device 500 is configured such that at least during operation of the device, the working end 91' of a particular tool 190' (that is accommodated in the passageway 150') and that projects distally from the distal end of the distal portion 135', is in this field of view. The field of view of the image acquisition unit 145' in this embodiment is about 120°, and this may be achieved, form example, by providing a suitable 120° convex lens at the distal end of the distal portion 135' in optical communication with the image acquisition unit 145'. In alternative variations of this embodiment, the image acquisition unit 145' may have a different field of view, for example greater than about 90°, for example 180°, or indeed much narrower FOV, for example 60°, or 50°, or 40°, or 30°, or 20° or 10°.

A suitable illumination arrangement 170' may be provided via the passageway 150', and comprises a light guide which for example may be in the form of a plurality of optical fibers accommodated within the probe member 20', having a proximal end configured for optical coupling to a suitable light source system 530, and a distal end via which illuminating light from the light source is transmitted to the tissue being worked on during operation of said device. Thus, the light guide may comprise a multi-fiber wave guide, having, by way of non-limiting example, a diameter of between about 300 micron to about 350 micron accommodating about 3000 optical fibers or more.

Any suitably shaped tool may be inserted into the central passageway 150' such that a distal working end 91' of the tool may be projected into the tissue being worked on via the distal end 130'. Such a tool may comprise, for example, a suitable dental file or reamer, which may be made from nickel titanium or stainless steel for example.

Other tools which may be used via the central passageway 150', may include, by way of non-limiting example, a laser energy delivery system, such as a laser cutting tool, a grasping tool such as micro tongs or a magnetized grasping tool, inter alia, wherein the working portion of the tool projects distally from the distal end of the device at least during operation of the device.

Alternatively, such a tool may be a powered tool, for example a dental drill or reamer, and may comprise, for example, diamond drills or tungsten drills, configured for drilling into bone such as in the maxilla, for example. The working portion 91' of the tool, i.e. the portion of the tool that interacts with the dental tissues, projects distally away from the distal end of the distal end 130'.

Alternatively, the tool may comprise a syringe 540 having a syringe needle of suitable dimensions and flexibility that may be inserted into the central passageway 150' and optionally extend therethrough such that the working portion, i.e., the tip of the syringe needle comprising the syringe outlet, projects from the distal end 130', and enables a desired agent to be delivered to the area being worked on (and/or for fluids to be sucked therefrom) via the syringe at least during operation of the device. Such an agent may comprise, by way of non-limiting example, bone graft material, irrigating solutions, antibiotics, liquid filler, liquid sealant, and so on, inter alia.

As already mentioned, the tool may comprise, for example, a dental laser tool, and such tools are well known in the art. For example, a suitable laser light guide, such as for example one or a plurality of suitable optical fibers, may be passed through the central passageway 150' to the distal end 130', and the proximal end of the optical fiber(s) is optically coupled to a suitable laser radiation generator 550, for example an Erbium laser light source, via suitable optical couplers. Alternatively, the laser tool may comprise a hollow wave guide, coupled to the laser source, and sealed at the distal end thereof by a sapphire tip, which is shaped to direct the laser radiation in the required direction to the area to be treated, for example axially or at an angle to axis 23', where the distal end of the hollow wave guide is wedge-shaped at a suitable wedge angle. Such a hollow wave guide may be, by way of example, of diameter about 100 micron to about 160 micron.

In another example, the tool may be a suitable ultrasonic tool or an RHF cutting tool. Ultrasonic cutting tools are known in the art and may comprise, for example, a piezo electric or electromagnetic source for providing the high energy vibrations required for operation of the tool. Some examples of such ultrasonic cutting tools may include: the Enac device, produced by Osada (Japan); the Satalec device, produced by Acteon Group, (France); the EMS ultrasonic device, produced by EMS (Switzerland); the Varios 750 device, by NSK (Japan); the Miniendo II device produced by Sybron Dental (USA). RHF cutting tools are also known, for example diathermic devices (monopolar, bipolar, RHF) and can be used for cutting through dental soft tissues. By way of non limiting example, such a device may include the Erbotom 80 device, produced by ERBE (Germany).

Furthermore, additional tools including an irrigation and/or suction catheter may be provided via the passageway 150'.

In this embodiment, the distal end 130' is also optionally configured for use as a cutting or boring tool. For this purpose, a distal edge 133' projects beyond the distal end 130' of the probe, and the distal edge 133' may be sharp, serrated, or abrasive, and this feature of the device 500 is used by manually manipulating the device 500 to provide a material removal action with this edge in contact with a tissue surface, for example. Operation of this tool may be monitored in real time via the image acquisition unit 145' and system 520, which keeps the distal edge 133', i.e., the working end of the tool, in the field of view thereof by retracting the image acquisition unit 145' into the passageway until the distal edge 133' comes into view (FIG. 1a). The probe member 20', or at least the distal portion 135', may be made from a transparent material which further aids in monitoring the operation of the edge 133' with respect to tissue 300' that is being worked on by the tool.

In alternative variations of this embodiment, the distal edge 133' defines the distal end of the probe, and the working end of the tool is within the field of view of the image acquisition unit 145' by retracting the image acquisition unit 145' into the passageway until the distal edge 133' is within the FOV and comes into view. Alternatively, no retraction may be needed, and the image acquisition unit is provided with a very wide field of view, for example 180°.

Image data collected by the imaging system 520 may be communicated to image analysis and display unit 525, for example a computer, for analysis and display. The imaging system 520 may provide discrete images of the said internal surfaces as required, and/or may provide a sequence of such images in real time providing a video stream that may be viewed by the user of the device (typically a dental surgeon) and/or any other observer. Optionally, such images may also be recorded in a memory or any suitable recording device.

The device 500 may be fully disposable, i.e., may be made from materials that render the device disposable after use with one patient or that permit such disposability from an economic perspective, for example. Alternatively the probe member or at least the distal portion thereof are disposable, and are releasably connected to the hand piece 50' or the remainder of the probe member, respectively, in a suitable manner. Alternatively, the device, or the probe member, or at least the distal portion thereof, may be provided with a suitable sheath (not shown) for protecting the device from contamination during use, and the sheath is disposed of after use with a patient.

Alternatively, the device 500 may be sterilizable, for example by autoclaving, and components thereof sensitive to such sterilization are removable therefrom prior to any such operation.

According to a second aspect of the invention, there is provided a dental implant which while being particularly useful for implantation in the maxilla of a patient may also be particularly useful for implantation in the mandible of a patient.

Figure 2:
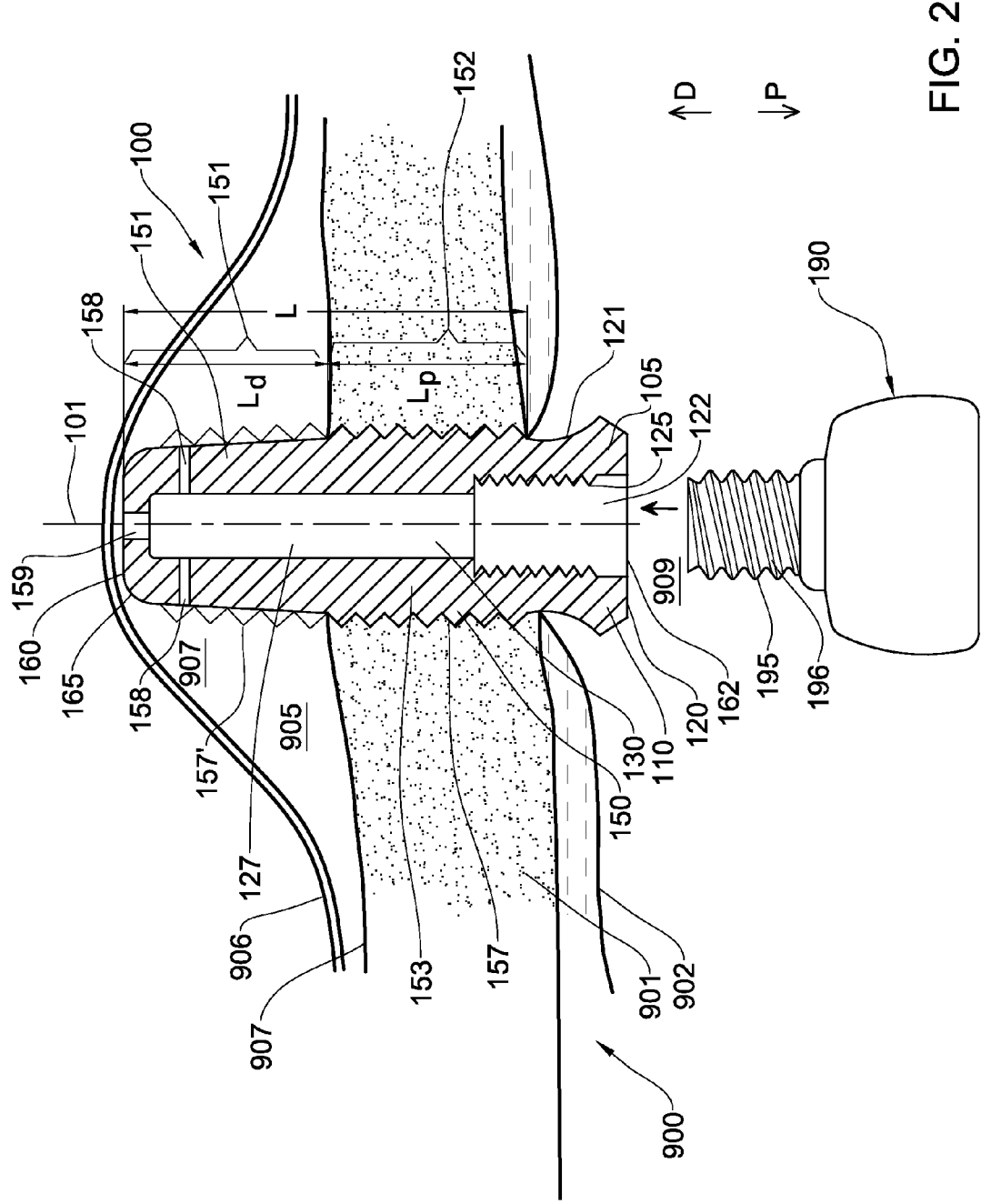
FIG. 2 illustrates, in transverse cross-sectional view, a dental implant according to a first embodiment of the invention.

Referring to FIG. 2, a first embodiment of a dental implant according to the second aspect of the invention, generally designated with the numeral 100, is in the form of a generally tubular body 105, comprising a proximal portion 110 having a proximal end 120, a distal portion 150 having a distal end 160, and a generally rectilinear lumen or passageway 130 longitudinally extending through the proximal portion 110 and the distal portion 150.

The proximal portion 110 is configured for enabling a prosthesis 190 having a prosthesis mounting arrangement 196 to be mounted to the implant 100, and thus comprises a head 121 that is configured for mounting therein the particular prosthesis 190 using any suitable prosthesis engagement arrangement. For example, such a prosthesis engagement arrangement may comprise an internal bore 122 comprising internal threads 125 that are configured to be engaged with the external threads 195 of the prosthesis mounting arrangement 196, which projects distally from the distal end of the prosthesis 190. It is evident to the skilled practitioner that other and different prosthesis engagement arrangements may be provided in the proximal portion 110 according to the specific configuration of the prosthesis mounting arrangement 196.

The distal portion 150 is configured for being implanted in the maxilla 900 of a patient, and comprises a proximal part 152 and a distal part 154. The distal portion 150 has a dimension L along the longitudinal axis 101 of the implant 100 of sufficient magnitude, such that in the implanted position of the implant 100, the distal part 154 of the distal portion 150, including the distal end 160, projects through the alveolar ridge 901 and away from the sinus floor 907 in the direction towards the sinus cavity 910, while the proximal part 152 is anchored in the bone of the alveolar ridge 901 of the maxilla 900. In the aforesaid "implanted position", the implant 100 is at its maximal desired distal position with respect to the maxilla, illustrated in FIG. 2, so that the proximal portion 110 is at the desired permanent position with respect to the maxilla 900 to receive the prosthesis 190.

The proximal part 152 is thus configured for being engaged and secured to the alveolar ridge 901, and in this embodiment comprises a cylindrical body portion 153 having self-tapping external threads 157 having a cylindrical outer profile and configured for cutting into the alveolar bone and securing the dental implant 100 with respect thereto. In alternative variations of this embodiment, the body portion 153 may instead be non-cylindrical, for example frustoconical or any other suitable shape, and/or the external threads 157 may instead be non-tapping, and/or the external threads may have a non-cylindrical outer profile, for example frustoconical or any other suitable shape. In any case, the external threads 157 may have any suitable cross-sectional profile, as is known in the art to secure the proximal part 152 in the alveolar bone.

Thus, the longitudinal length $L_p$ of the proximal part is correlated and generally corresponds to the depth of the alveolar ridge 901, up to the sinus cavity 905, and for example, this longitudinal length $L_p$ may be between about 2 mm and about 8 mm.

The distal part 154 has a longitudinal length $L_d$ that projects into the sinus cavity 906, and represents the minimum depth of the sinus augmentation that is formed by means of the dental implant 100, as will become clearer below.

Thus dimension L is the sum of longitudinal length $L_p$ and longitudinal length $L_d$. Distal part 154 is, in this embodiment, generally tubular, having a generally cylindrical outer form. In alternative variations of this embodiment, the distal part 154 may instead be non-cylindrical, for example frustoconical or any other suitable shape. Optionally, external threads 157 continue on the distal part 154, as shown in phantom lines 157' in FIG. 2.

Figure 3:
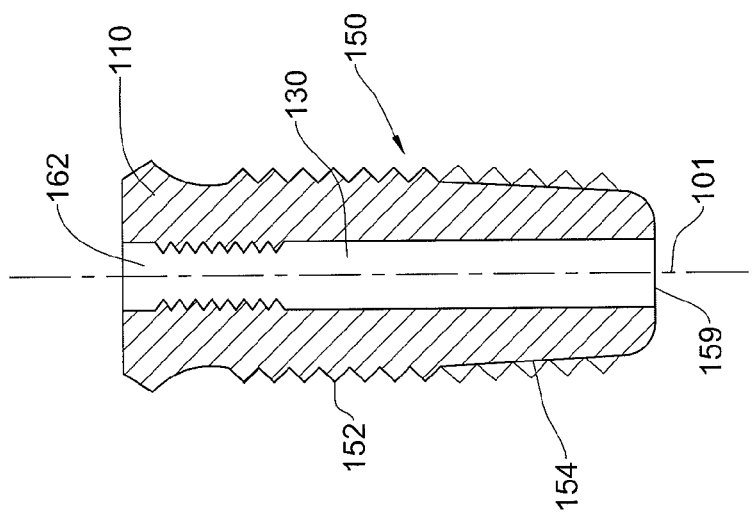
FIG. 3 illustrates, in transverse cross-sectional view, a dental implant according to a variation of the embodiment of FIG. 2.

Distal part 154 comprises a plurality of distal openings 158, 159 providing fluid communication between the passageway 130 and an outside 907 of the distal part 154. One or a number of openings 158, for example 2, 3, 4 or more openings, are provided around a periphery of the distal part 154 and are generally lateral-facing, though one or more such openings 158 may optionally have an axis through the respective opening that be inclined at least with respect to the longitudinal axis 101, and are located on the cylindrical wall 151 of the distal part 154, for example close to but proximal to the distal end 160. A single opening 159 is provided at distal end 160, aligned with the axis 101, though in alternative variations of this embodiment a plurality of such openings may be provided at distal end, and one or none such openings may be aligned with axis 101. The dental implant 100 also comprises a proximal opening 162, which provides fluid communication between the passageway 130 and an outside 909 of the proximal portion 110. In this embodiment, the well 122 forms a proximal part of the passageway 130, and is thus aligned with the axis 101, and a distal part 127 of the passageway 130, also aligned with the axis 101, has a smaller internal diameter than well 122. Thus, proximal opening 162 and distal openings 158, 159 provide fluid communication between an outside of proximal portion 110 and an outside of the distal part 154 via well 122 and distal part 127, i.e., passageway 130. As illustrated in FIG. 3, in an alternative variation of the first embodiment, the distal openings 158 are omitted, and part 154 only comprises a distal opening 159 at distal end 160.

Furthermore, in the embodiments of FIG. 2 and FIG. 3, there is a direct line-of-sight (LOS) between the proximal opening 162 and distal opening 159 along axis 101. In alternative variations of the embodiments of FIGS. 2 and 3, in which a plurality of distal openings may be provided at the distal end 160, there is a direct line-of-sight (LOS) between the proximal opening 162 and one or each one of a portion of, or indeed all of, such distal openings. In these or other alternative variations of the embodiments of FIGS. 2 and 3, a plurality of separate passageways may be provided in the body of dental implant, each providing fluid communication between outside 909 and outside 907, via one or more openings 158 and/or 159, and via common proximal opening 162, or via one of a plurality of proximal openings provided at or near the proximal end 160 or via one of a plurality of proximal openings provided into well 122.

In alternative variations of the embodiments of FIGS. 2 and 3, the distal end, and/or a section of the distal part 154 close to the distal end 160 may be formed as a mesh or net, wherein the openings of the mesh or net constitute said distal openings.

Distal end 160 has a blunt form, and is devoid of any sharp, serrated or otherwise cutting surfaces, edges, protrusions or other surface features that are otherwise configured for cutting, slicing or puncturing tissue, especially tissue such as the sinus membrane 906 of the maxilla 900. In the illustrated embodiment, the distal end 160 has a relatively flat surface, with a beveled edge 165, though in alternative variations of the first embodiment the distal end may be convexly curved or have any other suitable shape that minimizes risk of damage to the sinus membrane when in contact with the distal end 160 and when raised thereby.

The dental implant 100 according to the first embodiment may be formed as a unitary piece or from several components suitably joined together, and made from one or more suitable and biocompatible materials, for example titanium or stainless steel.

The implant 100 may optionally be configured for sealingly closing the passageway 130, for example by means of a sealing fit between the prosthesis 190 (or a temporary abutment that is engaged to the implant 100 during the healing process).

Alternatively, the passageway 130, or at least the distal part 127 thereof, may be sealed independently of the prosthesis 190 (or temporary abutment), thereby closing fluid communication between the outside 907 and the outside 909, preventing ingress of contaminants to the maxilla from the intra oral cavity 970, and preventing egress of bone tissue, bone graft material, etc from the maxilla implantation site. Thus, referring to FIG. 2(a), in one such embodiment a plug 106 is provided that is selectively and sealingly engageable with the distal part 127 of central passageway 130 via complementary screwthreads 111, 112 respectively. Plug 106 may comprise a slit 113 that aids the user in manipulating the plug 106 to selectively insert the same into the distal part 127, and thereafter rotate the plug 106 to engage the same therein.

Figure 2C:
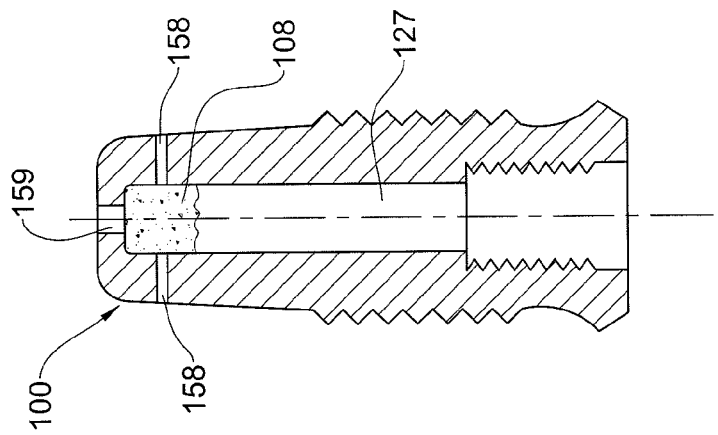
FIG. 2(c) illustrates, in transverse cross-sectional view, a further alternative sealing arrangement to dental implant shown in FIG. 2.
Figure 2B:
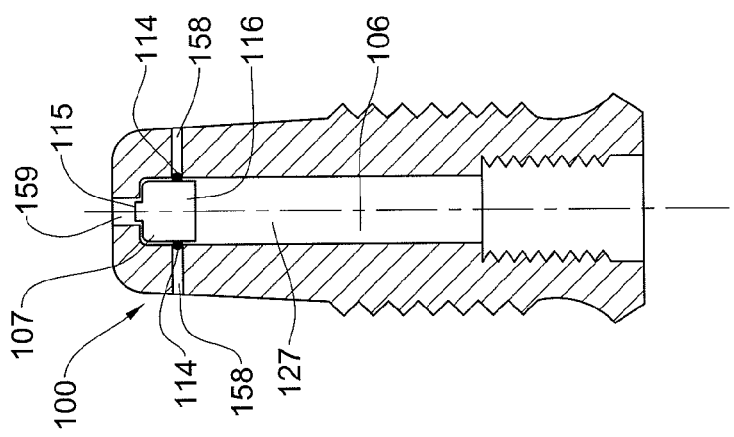
FIG. 2(b) illustrates, in transverse cross-sectional view, another alternative sealing arrangement to dental implant shown in FIG. 2.

Alternatively, and referring to FIG. 2(b), in another such embodiment a plug 107 is provided that is selectively and sealingly engageable with the distal end of distal part 127 of central passageway 130. Plug 107 comprises a plurality of projections 114 and 115 resiliently formed on or mounted to the outer cylindrical surface and distal end, respectively, of the plug body 116. The projections 114 and 115 are configured for being inwardly deflected as the plug 107 is moved distally in the distal part 127 and spring back and are at least partially accommodated in corresponding distal openings 158, 159, respectively when the plug 107 reaches the distal end of the distal part 127, thereby sealing the distal openings 158, 159 and distal part 127.

Alternatively, and referring to FIG. 2(c), in another such embodiment a plug 108 is formed in situ by selectively injecting a suitable sealing material, such as for example dental glue, to thereby sealingly plug the distal end of distal part 127 of central passageway 130, either proximal to the distal openings 158, 159 or including distal openings 158, 159.

Figure 4:
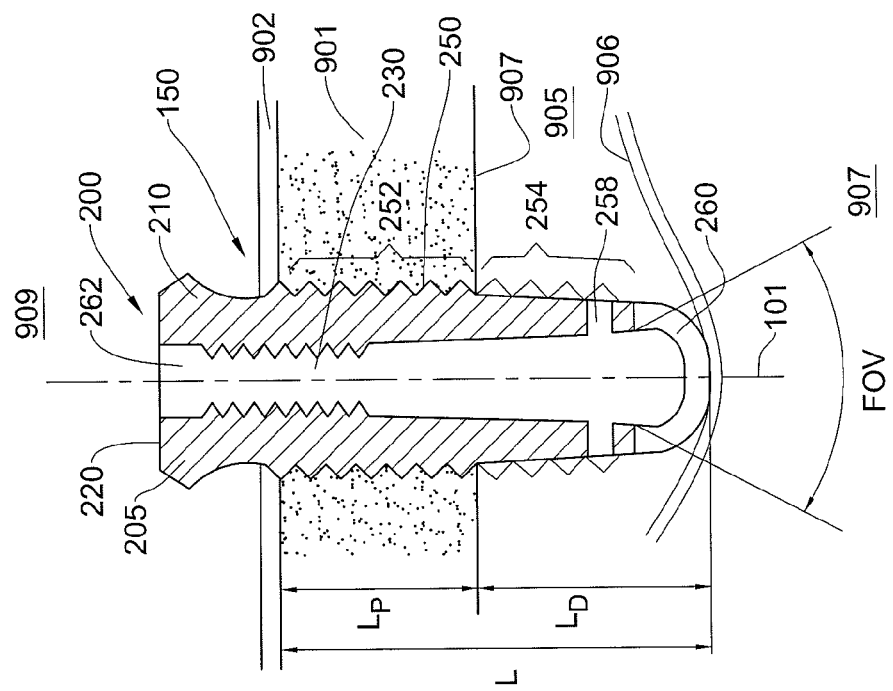
FIG. 4 illustrates, in transverse cross-sectional view, a dental implant according to a second embodiment of the invention.

A second embodiment of the dental implant according to the second aspect of the invention, generally designated with the reference numeral 200, is illustrated in FIG. 4 and comprises all the elements and features of the first embodiment of FIG. 2 and at least some alternative variations thereof, though with some differences as will become clearer herein. Thus, implant 200 is also in the form of a generally tubular body 205, comprising a proximal portion 210 having a proximal end 220 and opening 262, a distal portion 250 comprising a proximal part 252 and a distal part 254, and having a distal end 260 and one or more distal openings 258, and a lumen or passageway 230 longitudinally extending through the proximal portion 210 and the distal portion 250, respectively corresponding to tubular body 105, proximal portion 110, proximal end 120, opening 162, distal portion 150, proximal part 152, distal part 154, distal end 160, distal openings 158, and passageway 130 of the first embodiment, mutatis mutandis.

However, in the second embodiment, there is no distal opening at the distal end 260 corresponding to distal opening 159 of the first embodiment, and thus, proximal opening 262 and distal openings 258 provide fluid communication between an outside of proximal portion 210 and an outside of the distal part 254 via passageway 230.

In the second embodiment, at least the closed distal end 260 is made from a transparent material, that is also biocompatible, such as for example glass or a suitable transparent polymer, or any suitable material—for example a sapphire stone—thereby providing a direct line-of-sight (LOS) from the proximal opening 262 and through the distal end 260 along axis 101. The remainder of the implant 200 may be made from an alternative material, for example titanium.

In the second embodiment, the distal end 260 also has a blunt form, and is devoid of any sharp, serrated or otherwise cutting surfaces, edges, protrusions or other surface features that are configured for cutting, slicing or puncturing tissue, especially tissue such as the sinus membrane 906 of the maxilla 900, similarly to the distal end 160 of the first embodiment of the implant 100, mutatis mutandis. In the second embodiment illustrated in FIG. 4, the distal end 260 has a convex surface, for example a hemispherical surface, and thus acts an optical lens increasing the field of view (FOV) when observing the outside of the distal end 260 from inside the passageway 230. The curvature of the distal end 260 may be chosen to be such as to provide any desired FOV, for example the distal end may be fully hemispherical, thereby providing a FOV similar to that of a fish-eye lens with a FOV of about 180°. In alternative variations of this embodiment, the distal end may be configured for providing a FOV of about 120°, or 90°, or 50°, or any other desired FOV. In alternative variations of the second embodiment the distal end 260 may have a relatively flat surface, with a beveled peripheral edge, or have any other suitable shape.

The direct line of sight between the proximal end of the implant and the environment distal of the distal end provided by the implant according to the second aspect of the invention may also be useful in other dental procedures, such as for example when installing such an implant in the mandibular jaw in which the risks of damaging the inferior alveolar nerve in the mandibular canal are minimized by virtue of enabling the dental surgeon to view the implantation area via the implant.

As with the first embodiment, mutatis mutandis, the implant 200 may optionally be configured for sealingly closing the passageway 130, for example by means of a sealing fit between the prosthesis 190 (or a temporary abutment that is engaged to the implant 100 during the healing process), or independently thereof, thereby closing fluid communication between the outside 907 and the outside 909, preventing ingress of contaminants to the maxilla from the intra oral cavity 970, and preventing egress of bone tissue, bone graft material, etc from the maxilla implantation site. Thus, suitable plugs, for example similar to plugs 106, 107, 108 disclosed for the first embodiment may also be used for the embodiment of FIG. 4, mutatis mutandis, with the required changes to enable compatibility therewith. For example, a variation of the plug 107 may be used with implant 200 by removing projection 115.

According to a third aspect of the invention, there is provided a procedure for installing a dental implant in the maxilla of a patient, and FIGS. 5(a) to 5(f) illustrate a first embodiment of such a dental implant installation procedure, which also includes a concurrent sinus augmentation procedure, according to the third aspect of the invention.

Figure 5A:
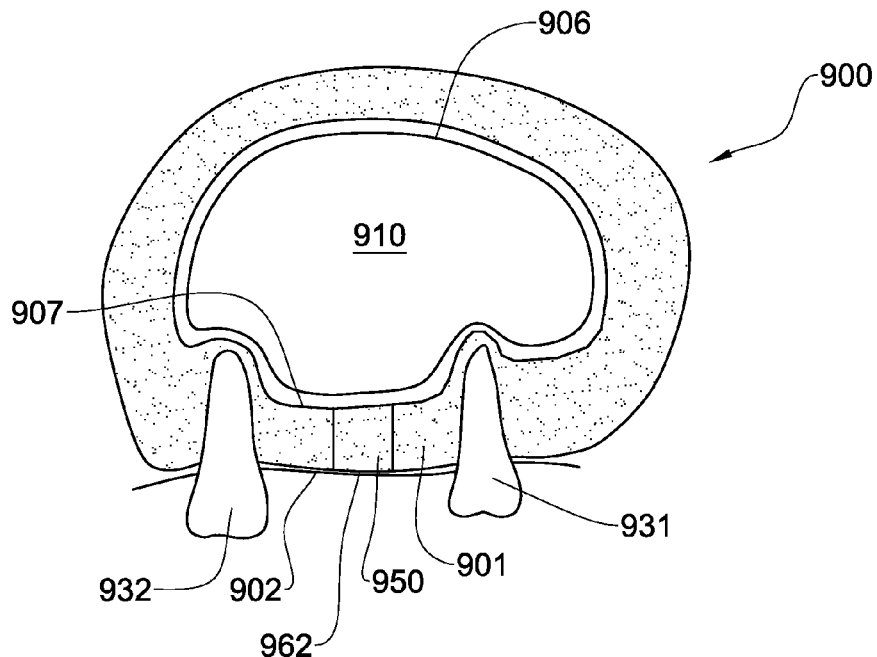
FIG. 5(a) illustrates, in transverse cross-sectional view, a step of a dental implant installation procedure according to a first embodiment of the invention.

Referring first to FIG. 5(a), a cross-section of a patient's maxilla 900 includes a maxillary sinus 910 having a sinus membrane 906, which is also interchangeably referred to as the membrane, the subantral membrane or the Schneiderian membrane. By way of illustrative, non-limiting example, a pair of existing teeth 931, 932 are shown on either side of the implantation site 950 where it is desired to install a dental implant, and where the thickness of the bony wall of the alveolar ridge 901 at the crest of the maxilla is initially insufficient for anchoring the dental implant. Of course, in particular applications of the implant installation procedure of the invention, one or both such adjacent teeth may be missing. In any case, this boney wall thickness may be the original thickness of the alveolar ridge when a real tooth existed at the implantation site 950, or the original bone thickness may have been reduced due to bone having been resorbed, as is often the case after teeth are removed from the maxilla.

Figure 5B:
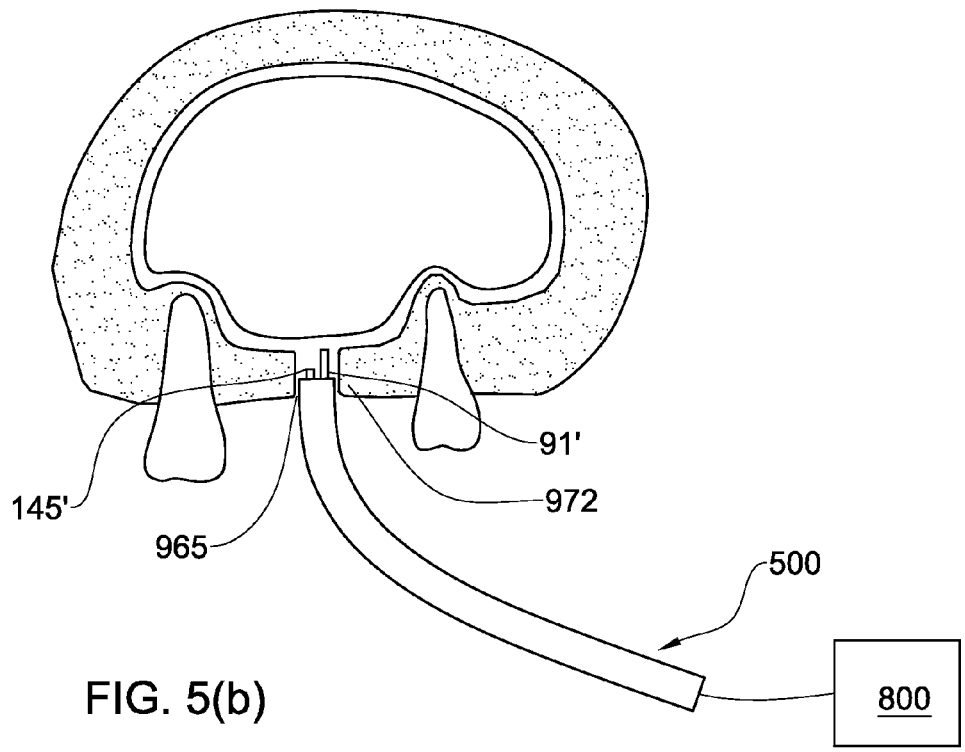
FIG. 5(b) illustrates, in transverse cross-sectional view, another step of a dental implant installation procedure according to a first embodiment of the invention.

Referring to FIG. 5(b), the first step in the dental implant installation procedure comprises cutting a window 972 in the crest or occlusal-facing gum tissue 902 where the implant is to be installed, and the gum tissue may be removed or pulled back. This window 972 is cut using the device 500 (optionally in conjunction with one or more of systems 520, 525, 530, 540, 550, collectively referred to as system 800—see FIG. 1) of the invention according to the first aspect of the present invention, for example. Alternatively, any suitable traditional tool may be used for creating the window, for example a scalpel.

Then, and also referring to the device 500 illustrated in FIG. 1, the distal portion 130' of the device 500 is brought into proximity with the crest 962 and a suitable tool having a working end 91', such as a dental drill or laser, for example, is provided via central passageway 150'. The tool removes, by drilling, ablation, or any other suitable bone and tissue material removal process, a bone section of the alveolar ridge 901 to create a channel 965. The material removal operation is under constant monitoring by the surgeon operating the device 500, via the image acquisition unit 145' and the image acquisition system 520 and display 525, while the area being cut and monitored is illuminated via illumination arrangement 170'. Bone tissue is removed until the sinus membrane 906 is exposed, and this point in the procedure is identified in a relatively easy manner since the area being operated on by the working end 955 of tool is in the field of view of the image acquisition unit 145' and thus in constant visual observation by the surgeon via the imaging system, which can provide the surgeon with a magnified video image in real time of this area.

Alternatively, the channel 965 may be created using conventional tools and procedure, for example as follows. An X-ray of the maxilla is first taken to determine the depth of the alveolar ridge 901, and a conventional tool such as for example a laser or mechanical drill is used to create a bore that is essentially a proximal part of the channel 965, to a depth about 1 mm less than aforesaid predetermined depth. A second tool is then used to knock out the remaining bone at the distal end of this bore, to thereby complete the channel 965 this second tool may also be a conventional tool used for this purpose, or alternatively device 500 may be used, suitably equipped with a tool that can carry out the tapping function. Alternatively, device 500 is used with a laser or drill tool to remove the remaining bone at the distal end of this bore under monitoring via the image acquisition unit 145'.

Figure 5C:
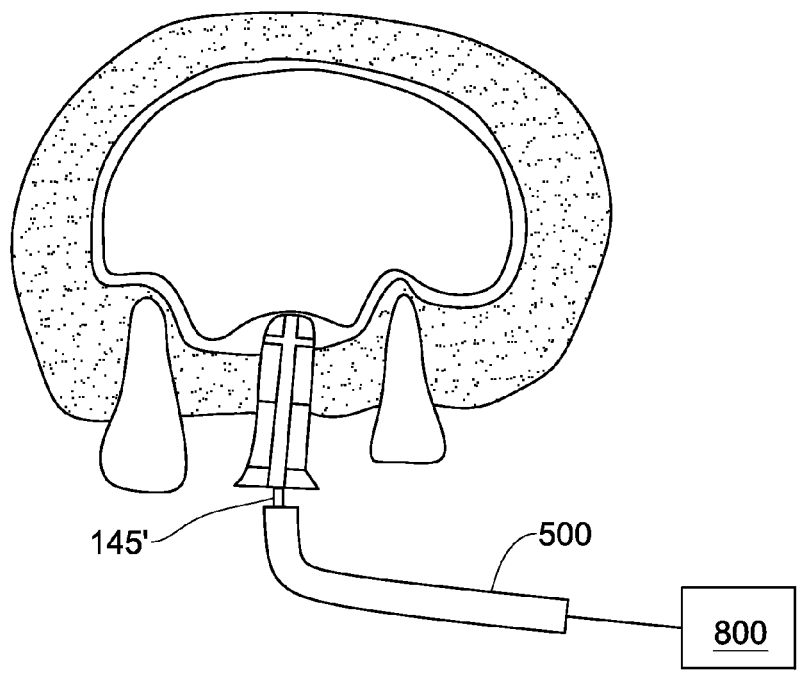
FIG. 5(c) illustrates, in transverse cross-sectional view, a further step of a dental implant installation procedure according to a first embodiment of the invention.
Figure 5D:
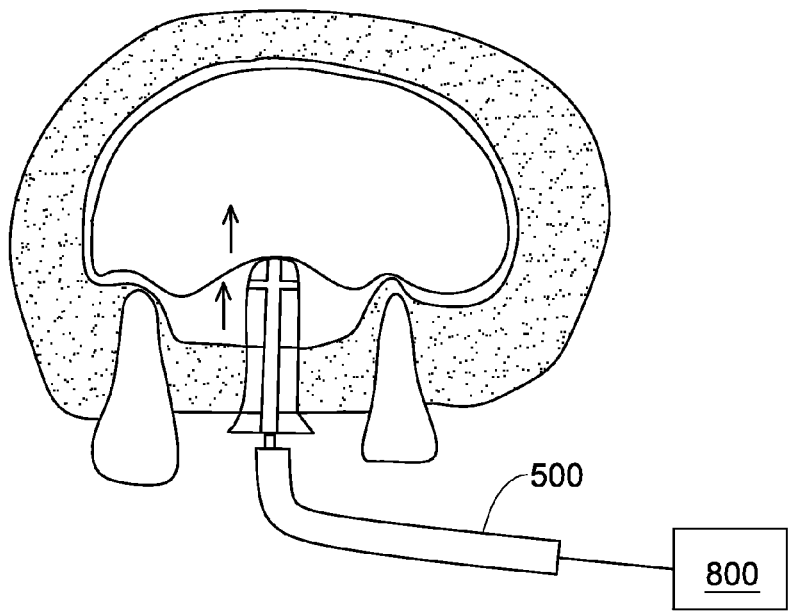
FIG. 5(d) illustrates, in transverse cross-sectional view, an even further step of a dental implant installation procedure according to a first embodiment of the invention.

In the next step, illustrated in FIG. 5(c), a dental implant according to the second aspect of the invention is installed in the maxilla 900 via the channel 965. In this figure, and by way of example, the dental implant 100 of FIG. 2 is partially inserted into channel 965 in the distal direction until the distal end 160 abuttingly contacts the sinus membrane 906. Concurrent with at least a latter part of this insertion process, device 500, in particular the via the image acquisition unit 145' and the image acquisition system 520 and display 525, are used for monitoring the insertion process. The image acquisition unit 145' is aligned with the axis 101 of the implant 100 such that the distal opening 159 is in the field of view of the image acquisition unit 145', enabling the user to visually see the area distal of the opening 159 via display 525. Optionally, the image acquisition unit 145' may be inserted into the passage 130 close to the distal opening 159 in embodiments where the image acquisition unit 145' can be accommodated in the passage 130; otherwise, the image acquisition unit 145' can be used for obtaining images from outside of the proximal end 160 of the implant.

Thus, it is readily apparent to the user when contact is made between the distal end 160 and the sinus membrane 906. Thereafter, the dental implant 100 is further inserted distally into the maxilla in an incremental manner, and as the distal end projects distally further and further into the maxilla 900, the distal end 160 pushes against the sinus membrane 906 and gently and directly lifts mechanically, the sinus membrane 906 from the maxillary sinus floor 907, and thereby distally displaces the sinus membrane 906 to create space 905.

At least a majority of the displacement of the sinus membrane 906, at least in the vicinity of the distal end 160, is carried out concurrent with and responsive to the distal end 160 being incrementally projected into the sinus cavity, and this progress may be continuously monitored using device 500, thus minimizing risk of damage to the sinus membrane 906. For example, as the sinus membrane 906 is displaced, it may become stretched at some point, and concurrently undergoes a blanching as blood drains from the membrane's blood vessels. This blanching can be observed by means of the device 500, in particular the image acquisition unit 145', as a change in color of the membrane seen via opening 159 from a reddish color to a whitish colour, and provides an indication of the stress that is being applied to the sinus membrane 906. Thus, the user can stop the implant insertion procedure if it becomes apparent via the blanching that the sinus is stretched and that further stretching may cause the membrane to rupture. In such a case, the implant may be replaced with another implant having a shorter distal part 154 which will not require such stretching of the membrane.

However, to avoid the need for replacing the dental implant in the first place, a probe having a blunt distal end may be inserted into the channel 965 prior to installation of the implant. The probe may be in the form of a tool that is provided via the central passageway 130' of the device 500 and is controllably projected past the distal end 133' of the device 500 such as to displace the membrane 906 in a similar manner to that anticipated for the implant 100, while being monitored via the image acquisition unit 145'. When the sinus membrane becomes blanched, the corresponding projection of the probe distal end into the sinus cavity is recorded, and this provides at least a rough estimate for the dimension $L_d$ of the distal part 154. Thereafter, a suitable implant 100 having this dimension $L_d$ for the distal part 154 is used for the rest of the procedure.

Thus, any potential damage to the sinus membrane 906 can be easily spotted by the user during the procedure via the image acquisition unit 145' and imaging system, since at least a part of the sinus membrane 906 is in the field of view of the image acquisition unit. In such circumstances the insertion of the implant may be interrupted, and the implant removed so that the sinus membrane may be repaired. At this point, or earlier, if there is detected a rupture, tear or other damage to the sinus membrane, this may be repaired by overlaying a collagen membrane over the damaged sinus membrane, for example. This repair may also be carried out using the device 500, wherein the collagen membrane is manipulated into place over the damaged area via a suitable tool provided via the device 500, while monitoring the repair procedure via the image acquisition unit 145'. Thereafter, the implant may again be inserted into the maxilla.

Otherwise, and referring to FIG. 5(*d*), the implant 100 is fully inserted into the maxilla 900 so that the proximal portion 110 is in the desired position, seated on the gingiva 902 of the maxilla 900 (see also FIG. 2). Thus, the distal part 254 projects a distance $L_d$ into the sinus cavity, similarly and concurrently displacing a corresponding portion of the sinus membrane 906.

In the next step, illustrated in FIG. 5(*e*), a suitable bone graft material is introduced in the space 905, and this may be done in a variety of ways.

In one example, bone graft material in the form of BMP or other liquid bone substitute material is injected directly into the space 905 via a suitable syringe 550, in which the syringe needle in the form of delivery hose 955 (which may be flexible) is coupled to the opening 162 of the implant 100, via the fluid communication provided by passage 130 and openings 158, 159.

Alternatively, the device 500 may be used for delivering the bone graft material into space 905. In this case, the device 500 is coupled with a syringe, in which a flexible syringe delivery needle or hose is accommodated in the central passageway 150' of the device, and the delivery end of the needle or hose projects distally from distal end of the device 500 and is coupled to the passage 130. In such a case, the injection process may optionally be monitored via the image acquisition unit 145'.

At the end of the process of providing bone graft material, the passage 130 may optionally be left open, or alternatively may be sealed in a number of ways. For example, a temporary abutment may be engaged to the dental implant in a similar manner to that intended for the prosthesis 190, thereby closing the opening 162. Alternatively, a suitable plug, or a sealing material such as for example a dental adhesive or filler may be inserted in the passage 130 via opening 162 to seal the passage 130, for example as illustrated in FIG. 2(*a*), 2(*b*) or 2(*c*).

The bone graft material that is delivered to the space 906 forms a sinus augmentation, with the dental implant in situ, and the dental implant is anchored in place. Residual bone graft material left in the passage 130 and openings 158, 159 further enhance the anchoring of the implant, wherein the sinus augmentation is allowed to heal and for the material in the space 905, passage 130 and openings 158, 159 to become fully integrated with the boney tissues of the maxilla. After the healing process, the abutment may be removed if one was mounted to the implant, and a suitable prosthesis 190 is mounted to the implant, as illustrated in FIG. 5(*f*).

The implant installation procedure of FIGS. 5(*a*) to 5(*f*) may be applied to the implant embodiment of FIG. 3 in substantially the same manner as disclosed above for implant 100 and FIGS. 5(*a*) to 5(*f*), mutatis mutandis, with the difference that delivery of bone graft material is via distal opening 159 only.

The implant installation procedure of FIGS. 5(*a*) to 5(*f*) may be applied to the implant embodiment of FIG. 4 in substantially the same manner as disclosed above for implant 100 and FIGS. 5(*a*) to 5(*f*), mutatis mutandis, with two main differences. One difference is that delivery of bone graft material is via lateral distal openings 259 only. Another difference is that monitoring of the sinus membrane during insertion of the implant, and subsequent thereto, is via the transparent distal end 260. In an alternative variation of the embodiment of FIG. 4, in which distal end 260 also comprises one or more distal openings, the bone graft material may also be provided via these openings, and/or monitoring may also be accomplished via these openings in addition to the transparent distal end itself.

While the implant installation procedure has been described above with respect to the sinus cavity, it also applies, mutatis mutandis, to installing a dental implant with a corresponding "nasal elevation" or "nasal augmentation" in the nasal cavity (nasal fossa), for example for replacing missing upper incisors and/or canines.

A second embodiment of the dental implant installation procedure according to the third aspect of the invention is illustrated in FIGS. 6(a) to 6(d) and comprises all the elements and features of the first embodiment of FIGS. 5(a) to 5(f) and at least some alternative variations thereof, though with some differences as will become clearer herein.

Figure 6A:
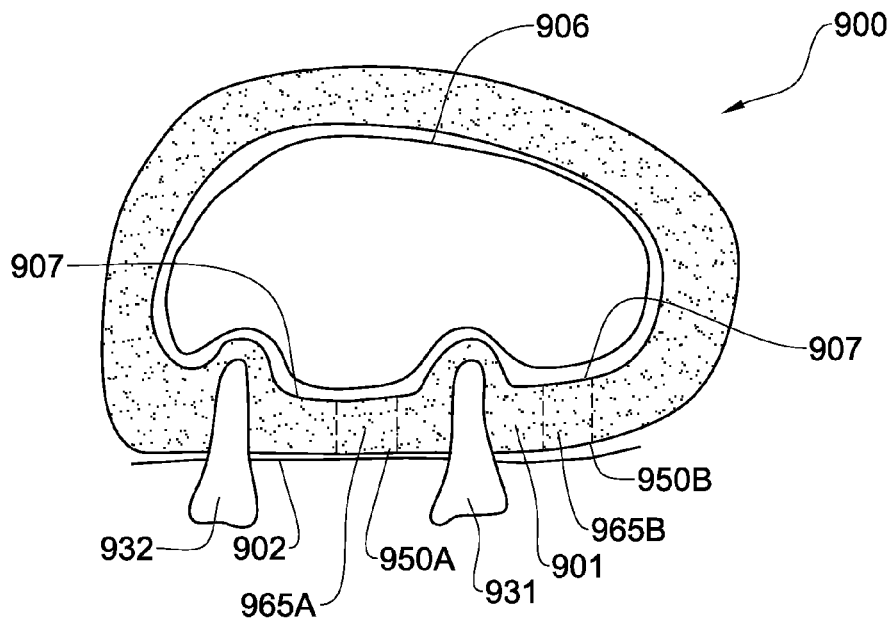
FIG. 6(a) illustrates, in transverse cross-sectional view, a step of a dental implant installation procedure according to a second embodiment of the invention.
Figure 6B:
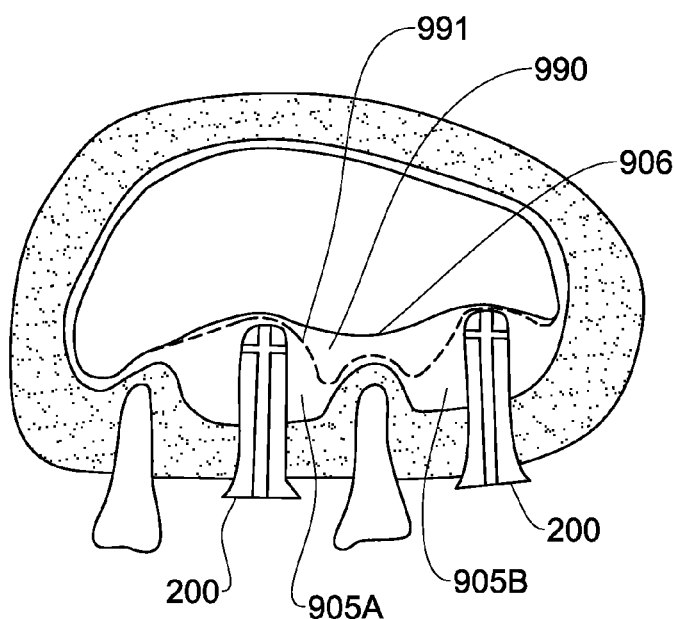
FIG. 6(b) illustrates, in transverse cross-sectional view, another step of a dental implant installation procedure according to a second embodiment of the invention.

In the procedure illustrated in FIGS. 6(a) to 6(d), the two dental implants are installed in the maxilla, and a contiguous sinus augmentation is provided for both implants. Referring first to FIG. 6(a), two implantation sites, 950A, 950b are identified in the maxilla 900, the first site 950A is in-between existing teeth 931, 932, while the second site 950B is on the other side of tooth 931. Of course, in other particular applications of the implant installation procedure according to the second embodiment of the invention, one or both such adjacent teeth may be missing, and/or the procedure may be extended to additional implantation sites in proximity to one another.

Then, at each site 950A, 950B, a respective channel 965A, 965B is created, in a similar manner to that disclosed above for channel 965 of the first embodiment, mutatis mutandis, for example in conjunction with FIG. 5(b). This is then followed by installation of an implant 200 at each of the sites 950A, 950B, in a similar manner to that disclosed above with respect to channel 965, for example with reference to FIGS. 5(c) and 5(d), mutatis mutandis, though the dimension L or $L_d$ for each implant 200 may be different. The implants may be installed in succession, or concurrently, in the latter case, each implant being alternately projected incrementally in direction towards the sinus cavity. However, since the two implants are in abutment with the sinus membrane 906 and directly raising the same from two spaced positions with respect to the sinus floor, a relatively larger space 990 is created than would be the case of the simple sum of the spaces 905A, 905B that could be created by each individual implant in the absence of the other, as indicated by the phantom line 991 in FIG. 6(b).

Figure 2A:
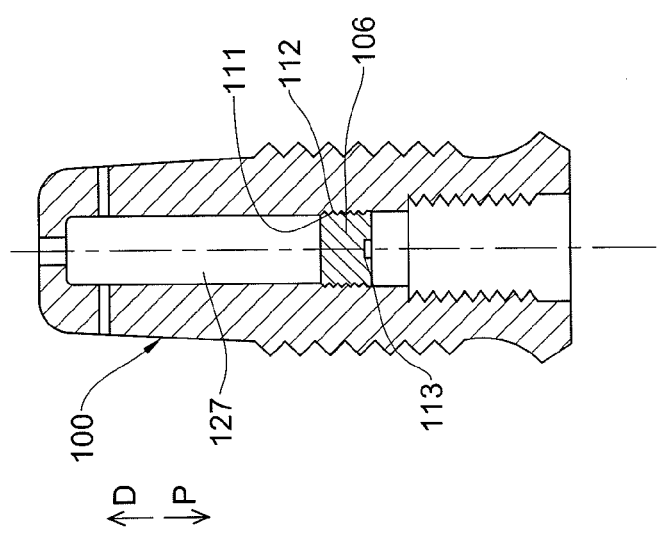
FIG. 2(a) illustrates, in transverse cross-sectional view, an alternative sealing arrangement to dental implant shown in FIG. 2.
Figure 5E:
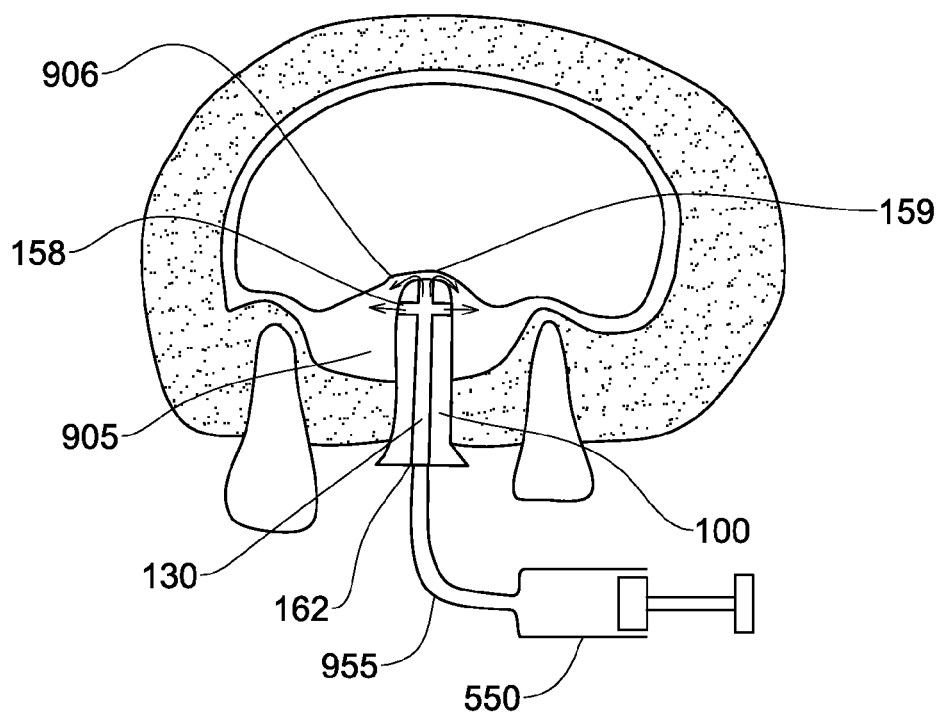
FIG. 5(e) illustrates, in transverse cross-sectional view, another further step of a dental implant installation procedure according to a first embodiment of the invention.
Figure 5F:
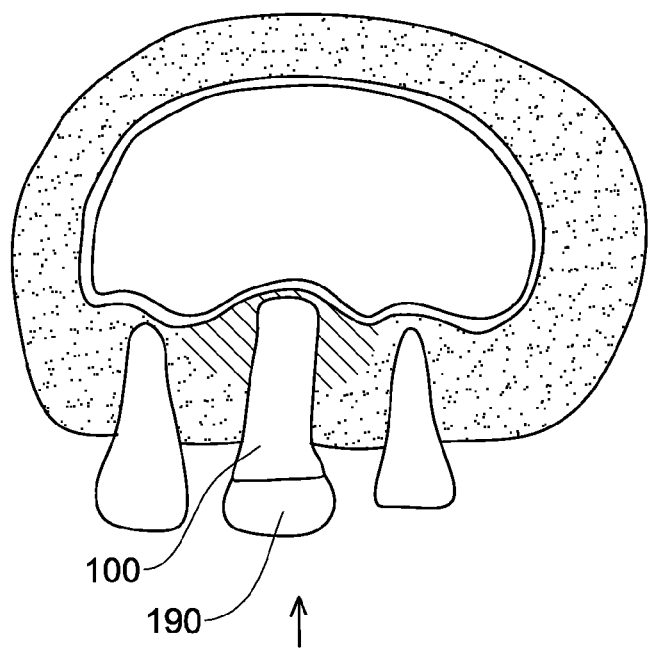
FIG. 5(f) illustrates, in transverse cross-sectional view, an even further step of a dental implant installation procedure according to a first embodiment of the invention.
Figure 6C:
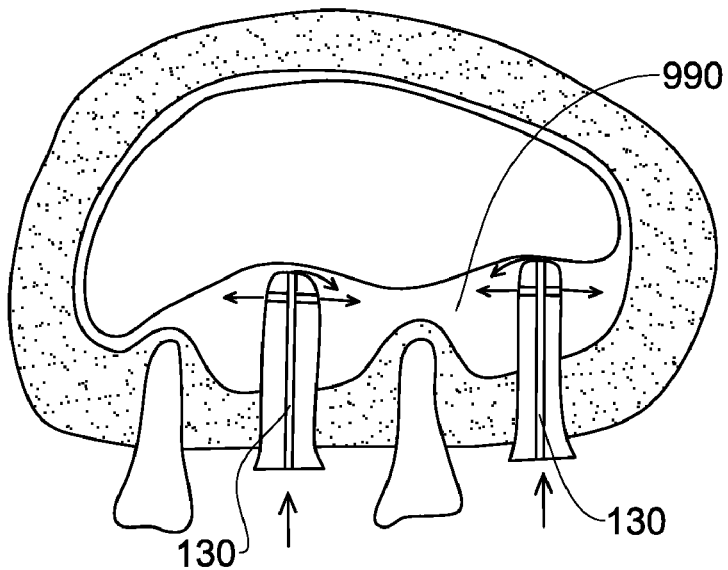
FIG. 6(c) illustrates, in transverse cross-sectional view, a further step of a dental implant installation procedure according to a second embodiment of the invention.
Figure 6D:
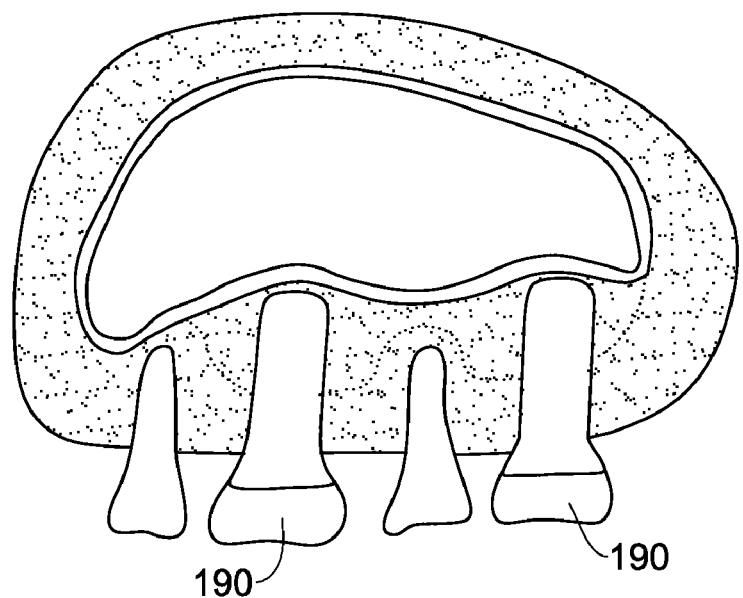
FIG. 6(d) illustrates, in transverse cross-sectional view, an even further step of a dental implant installation procedure according to a second embodiment of the invention.

In the next step, illustrated in FIG. 6(c), a suitable bone graft material is injected into cavity 990 via the passageway 130 of each implant 200, each in a similar manner to that disclosed above for the first embodiment, mutatis mutandis, for example with reference to FIG. 5(e), and optionally, the respective passages 130 may be sealed, for example as disclosed above with respect to FIGS. 2(a) to 2(c), mutatis mutandis. This creates a contiguous sinus augmentation including both implants 200 anchoring the implants. The sinus augmentation is allowed to heal and to become fully integrated with the boney tissues of the maxilla. After the healing process, the abutment may be removed if one was mounted to the implant, and a suitable prosthesis 190 is mounted to each implant, as illustrated in FIG. 6(d).

In a variation of the procedure illustrated in FIGS. 6(a) to 6(d), one of the two implants may be a conventional implant, i.e., in which said passage 130 is not present, but which comprises a non-cutting distal end, and in which a significant distal portion of the implant projects distally from the sinus floor, thereby displacing the corresponding part of the sinus membrane. In such an embodiment the injection of the bone graft material is via only the other implant 200, which thereby fills the whole space created by the displacement of the membrane.

In the method claims that follow, alphanumeric characters and Roman numerals used to designate claim steps are provided for convenience only and do not imply any particular order of performing the steps.

Finally, it should be noted that the word "comprising" as used throughout the appended claims is to be interpreted to mean "including but not limited to".

While there has been shown and disclosed example embodiments in accordance with the invention, it will be appreciated that many changes may be made therein without departing from the spirit of the invention.

The invention claimed is:

1. A method for implanting a dental implant in a maxilla of a dental patient, the maxilla having a paranasal sinus cavity lined with a sinus membrane, the method comprising:
    (a) providing the implant, the implant comprising a proximal portion configured for enabling a prosthesis to be mounted thereto and having at least one proximal opening, and a distal portion having a distal end and at least one distal opening at or in proximity to said distal end, said distal portion configured for being implanted with respect to the maxilla, and further comprising at least one internal passage providing fluid communication between said at least one proximal opening and said at least one distal opening;
    (b) forming a channel through the alveolar ridge of the maxilla, extending from an outside of the maxilla to the sinus floor of the maxilla;
    (c) installing the dental implant in the maxilla in the dental implant's required implanted position by inserting the implant via said channel, and concurrently creating a first space between the sinus floor and the sinus membrane, wherein at least a majority of said first space is formed by the distal displacement of said sinus membrane responsive to said distal end being incrementally projected in a direction towards the sinus cavity until the implant is seated in said implanted position with respect to the alveolar ridge, and wherein fluid communication between the outside of the maxilla and said first space is provided via said at least one passage and said at least one distal opening; and
    (d) providing via at least one internal passage and said at least one distal opening suitable bone graft material to said first space to form a sinus augmentation, wherein said at least one internal passage provides a direct line of sight between said at least one proximal opening and said at least one distal opening,
wherein a part of the sinus membrane in abutment with or in proximity to said distal end is in the field of view of an image acquisition system, and
further comprising monitoring in real time, using said image acquisition system, the sinus membrane during the displacement, and halting the displacement of the sinus membrane when a change of a color of the sinus membrane from a reddish color to a whitish color is observed.

2. Method according to claim 1, further comprising the step of anchoring the dental implant in situ in said sinus augmentation.

3. Method according to claim 1, wherein said distal end comprises a blunt abutment portion, and placing the blunt abutment portion in abutting contact with said sinus membrane at least during a majority of the displacement of said sinus membrane.

4. Method according to claim 1, wherein in step (d) additional said bone graft material is provided to further displace said sinus membrane wherein to augment said first space with a second space that is at least partially filled with said bone graft material, wherein said sinus augmentation also includes said at least partially filled second space.

5. Method according to claim 1, further comprising the step of sealing said at least one internal passage.

6. Method according to claim 1, further comprising the step of mounting a suitable prosthesis to said implant.

7. Method according to claim 1, wherein step (b) comprises:
forming a window in the gingival of the maxilla; and
using a working end of a first tool, removing material from the bone of the alveolar ridge of the maxilla to form said channel extending from said window to said sinus floor, while monitoring said material removal process via a suitable image acquisition system.

8. The method according to claim 7, wherein said first tool and said image acquisition system are included in a suitable device, and wherein said image acquisition system and said tool working end are positioned in the device, and positioning said tool working end in the field of view of said image acquisition system at least during operation of the first tool.

9. The method according to claim 8, including hand manipulating the device by the user at least during part of the step of removing material from the bone of the alveolar ridge of the maxilla.

10. The method according to claim 8, wherein the step of providing via at least one internal passage and said at least one distal opening suitable bone graft material to said first space to form a sinus augmentation comprises injecting said bone graft material using a second tool included in said device.

11. Method according to claim 10, wherein said second tool is provided in the form of a syringe having a respective second tool working end in the form of a delivery hose having a distal opening, and wherein said second tool is used for injecting said bone graft material into said first space via said distal opening, and including monitoring said injection of graft material via said distal opening is in real time via said image acquisition system.

12. Method according to claim 1, wherein at least one said distal opening is at said distal end, and including placing said part of the sinus membrane in abutment with or in proximity to said distal end in the field of view of said image acquisition system via said distal opening at said distal end.

13. Method according to claim 1, wherein said distal end is transparent, and including placing said part of the sinus membrane in abutment with or in proximity to said distal end in the field of view of said image acquisition system via said transparent distal end.

14. Method according to claim 1, further comprising sealing said at least one passage.

15. A method for implanting at least two dental implants in a maxilla of a dental patient, the maxilla having a paranasal sinus cavity lined with a sinus membrane, the method comprising:
providing the at least two implants, each said implant comprising a proximal portion configured for enabling a prosthesis to be mounted thereto and having at least one proximal opening, and wherein at least one said implant comprises a distal portion having a distal end and at least one distal opening at or in proximity to said distal end, said distal portion configured for being implanted with respect to the maxilla and further comprising at least one internal passage providing fluid communication between said at least one proximal opening and said at least one distal opening;
for each said implant, forming a respective channel through the alveolar ridge of the maxilla, extending from an outside of the maxilla to the sinus floor of the maxilla;
installing each dental implant in the maxilla in each dental implant's required implanted position by inserting each implant via the respective said channel, and concurrently creating a first space between the sinus floor and the sinus membrane by displacing said sinus membrane from said sinus floor, wherein at least a majority of said sinus displacement is responsive to each said distal end being incrementally projected in a direction towards the sinus cavity in abutment with said sinus membrane, and wherein fluid communication between the outside of the maxilla and said first space is provided via said at least one passage and said at least one distal opening for each said dental implant; and providing via at least one internal passage and said at least one distal opening suitable bone graft material to said first space to form a sinus augmentation,
wherein said at least one internal passage provides a direct line of sight between said at least on proximal opening and said at least one distal opening, wherein a part of the sinus membrane in abutment with or in proximity to said distal end is in the field of view of an image acquisition system, and further comprising monitoring in real time, using said image acquisition system, the sinus membrane during the displacement, and halting the displacement of the sinus membrane when a change of a color of the sinus membrane from a reddish color to a whitish color is observed.

16. A dental implant installation procedure, including the step of projecting a distal end of a dental implant into one of the paranasal sinus cavity and the nasal cavity until the dental implant is in the dental implant's implanted position, concurrently directly displacing the respective sinus membrane or nasal cavity membrane from the respective cavity floor via contact between the distal end and the respective sinus membrane or nasal cavity membrane, and thereby forming a space between the respective sinus membrane or nasal cavity membrane and the respective cavity floor, while minimizing risk of damaging the respective sinus membrane or nasal cavity membrane, and introducing bone graft material into said space via a distal portion of the dental implant to, respectively, form a sinus augmentation or nasal augmentation defined in said space,
wherein said at least one internal passage provides a direct line of sight between said at least on proximal opening and said at least one distal opening,
wherein a part of the sinus membrane in abutment with or in proximity to said distal end is in the field of view of an image acquisition system, and further comprising monitoring in real time, using said image acquisition system, the sinus membrane during the displacement, and halting the displacement of the sinus membrane when a change of a color of the sinus membrane from a reddish color to a whitish color is observed.

* * * * *